United States Patent [19]
Nikoonahad et al.

[11] Patent Number: 5,224,482
[45] Date of Patent: Jul. 6, 1993

[54] ULTRASOUND HIGH VELOCITY FLOW CORRELATION MEASUREMENT USING CODED PULSES

[75] Inventors: Mehrdad Nikoonahad, San Francisco, Calif.; Erlvada A. Sivers, Elmhurst, Ill.

[73] Assignee: Kabushiki Kaisha Toshiba, Kawasaki, Japan

[21] Appl. No.: 682,515

[22] Filed: Apr. 8, 1991

[51] Int. Cl.$^5$ ............................................. A61B 8/06
[52] U.S. Cl. ........................... 128/661.08; 128/661.1; 73/861.06
[58] Field of Search ...................... 128/661.07, 661.08, 128/661.1; 73/861.25, 631, 861.06

[56] References Cited

U.S. PATENT DOCUMENTS

| | | | |
|---|---|---|---|
| 3,910,259 | 10/1975 | Sullivan | 128/661.07 |
| 4,413,531 | 11/1983 | Karplus et al. | 73/861.25 |
| 4,751,929 | 6/1988 | Hayakawa et al. | 128/661.08 |
| 5,078,146 | 1/1992 | Sato | 128/661.08 |

OTHER PUBLICATIONS

M. Nikoonahad et al., Ultrasound Transverse Flow Measurement with High Lateral Resolution, IEEE Ultrasonics Symposium, 1988.
M. Nikoonahad, A Possibility for Ultrasound Flow Measurement with Microscopic Resolution, 17th International Conference on Acoustical Imaging, Sendai, Japan.
M. Nikoonahad et al., High-Resolution Ultrasound Transverse Flow Measurement, Electronics Letters, vol. 24, No. 4, Feb. 18, 1988, pp. 205-207.
M. Nikoonahad et al., Pulse Compression Acoustic Microscopy Using SAW Filters, IEEE Transactions on Sonics and Ultrasonics, vol. SU-32, No. 2, Mar. 1985, pp. 152-163.
M. Nikoonahad et al., Pulse Compression Acoustic Microscopy at 750 MHz, Electronics Letters, vol. 19, No. 19, Sep. 15, 1983, pp. 782-784.
L. Hatle, Maximal Blood Flow Velocities-Haemodynamic Data Obtained Noninvasively with CW Doppler, Ultrasound In Medicine and Biology, vol. 10, No. 2, Mar./Apr. 1984, pp. 225-237.
C. Kimme-Smith et al., Processing Algorithms for Color Flow Doppler, IEEE, 1989.
D. H. Evans, A Pulse-Foot-Seeking Algorithm for Doppler Ultrasound Waveforms, Clin. Phys. Physiol. Meas., vol. 9, No. 3, 1988, pp. 267-271.
L. Hatle et al., Noninvasive Assessment of Atrioventricular Pressure Half-Time by Doppler Ultrasound, Circulation, vol. 60, No. 5, Nov. 1979, pp. 1096-1104.
D. J. Sahn et al., Ultrasound Doppler Methods for Calculating Cardiac Volume Flows, Cardiac Output, and Cardiac Shunts, Cardiovascular Clin., vol. 17, No. 1, 1986, pp. 19-31.
C. Kasai et al., Real-Time Two-Dimensional Blood Flow Imaging Using an Autocorrelation Technique, IEEE Transactions on Sonics and Ultrasonics, vol. SU-32, No. 3, May 1985, pp. 458-464.
J. M. Evans et al., An Analogue Mean Frequency Estimator for Quantitative Measurement of Blood Flow by Doppler Ultrasound, Clin. Phys. Physiol. Meas., vol. 8, No. 4, 1987, pp. 309-315.
O. Bonnefous et al., Time Domain Formulation of Pulse-Doppler Ultrasound and Blood Velocity Estimation by Cross-Correlation, Ultrasonic Imaging, vol. 8, 1986, pp. 73-85.

(List continued on next page.)

*Primary Examiner*—William E. Kamm
*Assistant Examiner*—George Manuel
*Attorney, Agent, or Firm*—Finnegan, Henderson, Farabow, Garrett & Dunner

[57] ABSTRACT

An ultrasound high velocity flow measurement apparatus uses cross-correlation between consecutive echoes of coded pulses which are matched filtered at the receiver to determine velocity profiles of flowing blood. Because coded pulses are used, the interval between two pulses can be made arbitrarily small, effectively removing the peak velocity limitation.

14 Claims, 5 Drawing Sheets

OTHER PUBLICATIONS

O. Bonnefous et al., Statistical Analysis and Time Correlation Processes Applied to Velocity Measurement, 1989 Ultrasonics Symposium, IEEE 1989, pp. 887–892.

V. L. Newhouse et al., A Technique for Increasing the Maximum Range-Velocity Product of Pulse Doppler Systems, pp. 355–358.

V. L. Newhouse et al., Analysis of Transit Time Effects on Doppler Flow Measurement, IEEE Transactions on Biomedical Engineering, vol. BME-23, No. 5, Sep. 1976, pp. 381–386.

R. McHugh et al., Blood Flow Detection by an Intersecting Zone Ultrasonic Doppler Unit, Ultrasonic Med. & Biol., vol. 7, No. 4, 1981, pp. 371–375.

B. Angelsen, A Theoretical Study of the Scattering of Ultrasound from Blood, IEEE Transactions on Biomedical Engineering, vol. BME-27, No. 2, Feb. 1980, pp. 61–67.

K. H. Ong et al., Slurry Flow Velocity, Concentration and Particle Size Measurement Using Flow Noise and Correlation Techniques, Measurement and Control, vol. 8, Nov. 1975, pp. 453–461.

P. J. Fish, Multichannel, Direction-Resolving Doppler Angiography, pp. 153–159.

C. Kasai et al., Real-Time Two-Dimensional Blood Flow Imaging Using an Autocorrelation Technique, 1985 Ultrasonics Symposium, pp. 953–958.

I. A. Hein et al., Accurate and Precise Measurement of Blood Flow Using Ultrasound Time Domain Correlation, 1989 Ultrasonics Symposium, IEEE 1989, pp. 881–886.

K. W. Ferrara et al., Estimation of Blood Velocity Using the Wideband: Maximum Likelihood Estimator, 1989 Ultrasonics Symposium, IEEE 1989, pp. 897–901 (Ferrara et al.).

R. C. Thor, A Large Time-Bandwidth Product Pulse-Compression Technique, IRE Trans. on Military Electronics, Apr. 1962, pp. 169–173.

R. O. Rowlands, Detection of a Doppler-Invariant FM Signal by Means of a Tapped Delay Line, J. Acoust. Soc. Am., vol. 37, No. 1, Apr. 1965, pp. 608–615.

C. E. Cook et al., Radar Systems, Academic Press, New York, 1967, pp. 130–172.

V. M. Ristic, Principles of Acoustic Devices, John Wiley and Sons, New York, 1983, pp. 52–81.

J. E. Wilhjelm, Coherent FM Doppler System, 1989 Ultrasonics Symposium, IEEE 1989, pp. 903–906.

M. Nikoonahad, New Techniques in Differential Phase Contrast Scanning Acoustic Microscopy, Acoustical Imaging, vol. 16, 1987, pp. 1–10.

ULTRASOUND HIGH VELOCITY FLOW CORRELATION MEASUREMENT USING CODED PULSES

BACKGROUND OF THE INVENTION

1. Field of the Invention

The present invention relates to an ultrasound flow measurement apparatus and, more particularly, to an ultrasound high velocity flow measurement apparatus using time domain correlation.

2. Background Information

A primary use of ultrasound high velocity flow measurement apparatus is for blood flow velocity measurement and two dimensional mapping of blood flow velocity. One conventional apparatus is known as an ultrasonic Doppler velocimeter. The Doppler velocimeter transducer emits a continuous or pulsed beam of ultrasound generally in the range of 1 to 10 MHz in peripheral and deep-lying vessels. The frequency of the returned signal, backscattered from moving red blood cells, is different from the frequency of the signal transmitted. The difference in frequency is known as the Doppler shift frequency, $\Delta f$, given by:

$$\Delta f = \frac{2fv \cos(x)}{c}$$

where f is the transmitted frequency, v is the velocity of blood, x is the angle between the ultrasound beam and flow direction, and c is the velocity of sound in tissue.

Because of the random motion of the blood particles within the flow and because of the velocity variation across the vessel, the Doppler signal has a spectrum with a finite width rather than a single frequency. The method of measurement utilizing the Doppler methodology is sensitive to velocity components that are parallel to the ultrasound beam but are relatively insensitive to flow components that are perpendicular to the ultrasound beam.

Another conventional apparatus used in performing the blood flow velocity measurement and profiling is known as a cross-correlation velocimeter. Ordinarily, in the conventional cross-correlation velocimeter, a single pulse is transmitted to a blood vessel from a transducer and the echoes are received before a second pulse is transmitted. Normalized cross-correlation is then used to determine a time shift $(t_2 - t_1)$ of a segment of the first echo with respect to a similar segment of a second echo of the second transmitted pulse. The magnitude of the velocity v of the blood at the distance corresponding to the penetration depth of a relevant segment of the first pulse is given by the following expression:

$$v = \frac{c(t_2 - t_1)}{2T_{PR} \cos(x)} \quad (1)$$

where c is the velocity of sound in the medium, $T_{PR}$ is a pulse repetition (PR) interval and x is the angle that the ultrasound beam makes with the blood vessel. This is shown in FIG. 1. The time difference $(t_2 - t_1)$ is determined by cross-correlating segments of two consecutive signals which carry the flow information. The pulse repetition interval is set by the depth at which the vessel is located in the body. Therefore, the larger the depth, the larger the pulse repetition interval. On the other hand, equation (1) illustrates that for a given $(t_2 - t_1)$, the larger $T_{PR}$ the smaller the velocity v that can be measured. Furthermore, when the velocity v is high, the larger $T_{PR}$ increases the chances for the signals from two successive signals to be de-correlated. This de-correlation results because either during the time $T_{PR}$ scatterers flow out of the ultrasound beam, or in the case of turbulent flow, due to the random nature of the flow, the scatterers change their relative position and therefore, the signal from two successive signals become de-correlated.

Thus, the use of a conventional cross-correlation scheme for measuring high velocities at large depths presents two conflicting requirements. One requirement is a large pulse repetition interval so that the echoes can be separated between two successive signals. The second requirement is a small pulse repetition interval so that the signals remain correlated.

The issue of de-correlation of signals is rather complex. De-correlation depends on the time repetition interval and the flow velocity. Beam geometry and diameter further play important roles in determining the de-correlation time.

For a Gaussian beam with full width of w, the maximum measurable velocity at a pulse repetition time of $T_{PR}$ is:

$$w/(3.5 \, T_{PR} \sin(x))$$

As shown in FIG. 2, when pulse repetition time of 200 microseconds is used, the maximum depth of the vessel has to be less than 150 mm inside the body. With this repetition time, a beam diameter of 1 mm yields a maximum measurable flow velocity of 2 m/s for a vessel that intersects the ultrasound beam at 45°. In cardiology or peripheral vascular applications of ultrasound, however, situations exist where measurements must be made with flow jets having velocities in excess of 10 m/s. Neither Doppler nor conventional cross-correlation schemes are capable of measuring such velocities.

The conventional cross-correlation velocimeter discussed above utilizes single, or uncoded, pulses. Coded pulses, or frequency modulated pulses with frequencies that increase or decrease with time, however can be used in ultrasound apparatus. Coded pulses historically have been used in radar and acoustic imaging systems in order to increase the signal-to-noise ratio. In the general radar system, a ramp-up coded pulse, which is a frequency modulated pulse that has a frequency increase with time, or a ramp-down coded pulse, which is a frequency modulated pulse that has a frequency decrease with time, is transmitted to a target, and a resultant reflected signal is subsequently decoded utilizing a ramp-down or a ramp-up, respectively, decoding matched filter. Utilizing coded pulses increases the signal-to-noise ratio because a matched filter can suppress all signals except the appropriately coded echoes.

SUMMARY OF THE INVENTION

Accordingly, it is an object of the invention to provide an ultrasound high velocity flow correlation measurement apparatus that can accurately measure the blood flow measurement at high velocities and at large depths simultaneously.

It is another object of the present invention to provide an ultrasound high velocity flow measurement apparatus that will improve the signal-to-noise ratio over that attainable by use of uncoded pulses.

Additional objects and advantages of the present invention will be set forth in part in the description that follows and in part will be obvious from the description or may be learned by practice of the invention. The objects and advantages of the invention may be realized and obtained by the methods and apparatus particularly pointed out in the appended claims.

To achieve the objects and in accordance with the purpose of the invention as embodied and as broadly described herein, an ultrasound high velocity flow measurement apparatus using time domain correlation comprises a modulator for producing at least two coded pulses, the at least two codes pulses being separated by a predetermined delay; a transducer for transmitting the at least two coded pulses to a measuring object; a receiver for receiving a returned echo signal from the measuring object; a decoder for decoding the returned echo signal and producing at least two decoded signals being separated by the predetermined delay; and a correlator for cross-correlating the two decoded signals and outputting a velocity profile of the measuring object.

BRIEF DESCRIPTION OF THE DRAWINGS

The accompanying drawings, which are incorporated in and constitute a part of the specification, illustrate a presently preferred embodiment of the invention and, together with the general description given above and the detailed description of the preferred embodiment given below, serve to explain the principles of the invention.

DESCRIPTION OF THE PREFERRED EMBODIMENT

Figure 1:
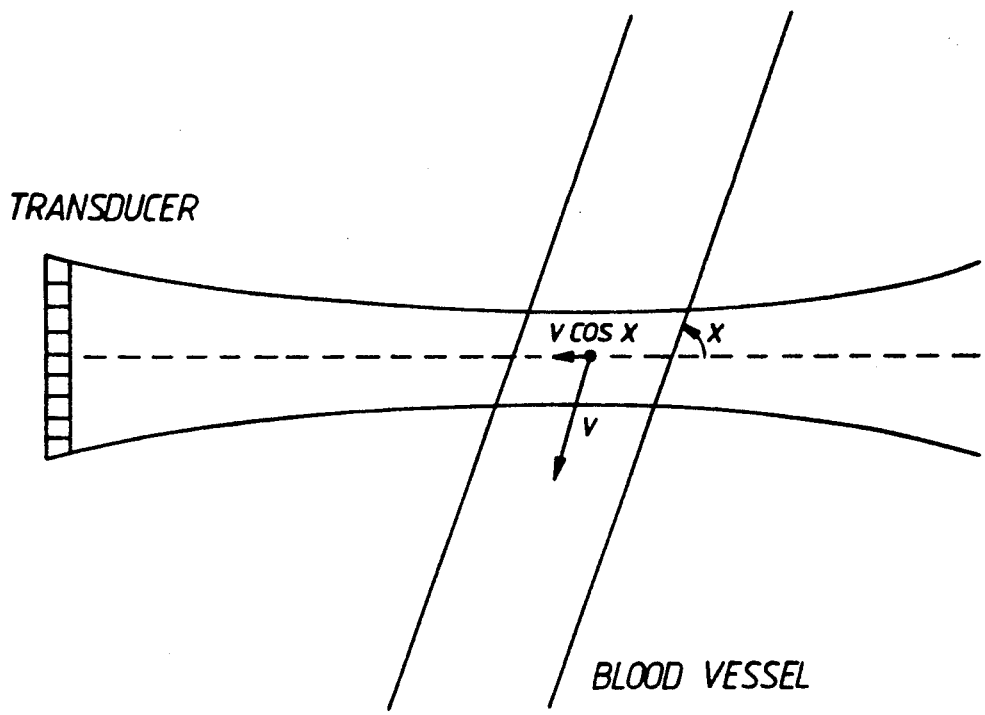
FIG. 1 illustrates the geometry of the transducer and the blood vessel for which the velocity profile is determined.
Figure 2:
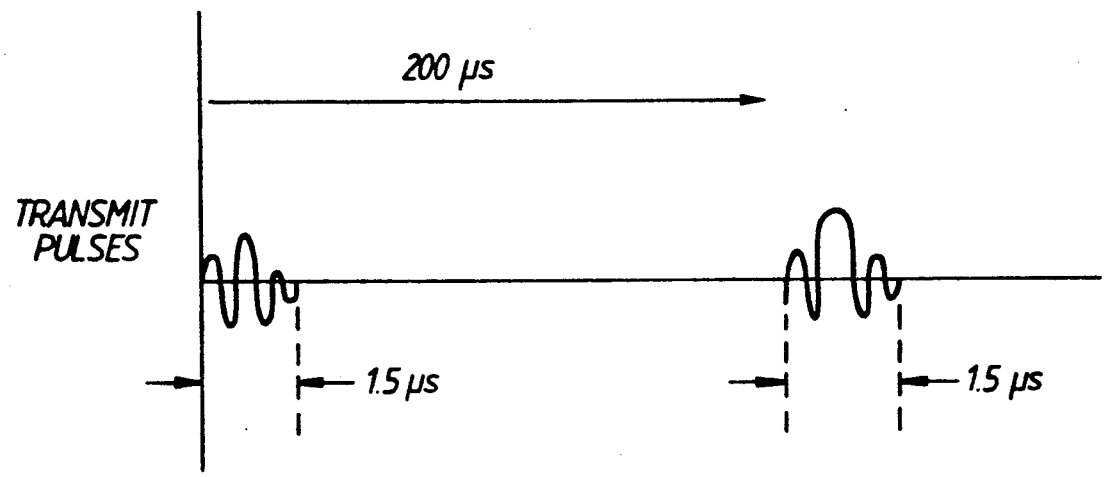
FIG. 2 illustrates two uncoded pulses separated by 200 μs.

Reference will now be made in detail to the presently preferred embodiment of the invention as illustrated in the accompanying drawings. Throughout the drawings, like reference characters are used to indicate like elements.

The present invention uses cross-correlation between consecutive echoes of coded pulses after match filtering to determine the velocity profile of flowing blood. As will be described in greater detail later, a preferred embodiment of the present invention transmits to the blood, in sequence, a coded pulse increasing in frequency and a coded pulse decreasing in frequency. The resultant reflected signals returning from the blood are subsequently separated by decreasing frequency decoding and increasing frequency decoding, respectively. The result from the decoding is pulses that can be cross-correlated to determine the velocity profile.

A method of velocity determination by cross-correlation according to a proposed embodiment of the present invention is based on the fact that inhomogenities in flowing blood give rise to distinctive echo patterns. As an inhomogenity moves through the ultrasound beam at an angle x with velocity magnitude v, the round trip time for pulses transmitted an interval $T_{PR}$ apart changes by the amount $(t_2 - t_1) = (2T_{PR}v \cos(x))/c$. This time change can be evaluated by cross-correlating segments of the echo from pulse 1 with the echo of pulse 2. If a band-limited, RF signal is digitized at a rate greater than the Nyquist rate, cross-correlation can be performed directly.

If $E_1(n\Delta t)$ is a sampled data for the first echo and $E_2(n\Delta t)$ is a sampled data for the second echo, these echoes are written as follows where $A(n\Delta t)$ is a time-dependent amplitude of the echo, $f_0$ is a carrier frequency, $\theta(n\Delta t)$ is a phase and $(t_2 - t_1)$ is a time shift:

$$E_1(n\Delta t) = A(n\Delta t) \cos(2\pi f_0 n\Delta t + \theta(n\Delta t)) \quad (2)$$

$$E_2(n\Delta t) = A(n\Delta t + t_2 - t_1) \cos(2\pi f_0 n\Delta t + t_2 - t_1) + \theta(n\Delta t + t_2 - t_1)) \quad (3)$$

The time shift $(t_2 - t_1)$ is equal to the value of $\epsilon$ for which Pearson's correlation coefficient $P(\epsilon)$ is equal to unity.

$$P(\epsilon) = \frac{N \sum_n^N E_1(n\Delta t) E_2(n\Delta t - \epsilon) - \sum_n^N E_1(n\Delta t) \sum_n^N E_2(n\Delta t - \epsilon)}{\sqrt{N \sum_n^N E_1^2(n\Delta t) - \left(\sum_n^N E_1(n\Delta t)\right)^2} \sqrt{N \sum_n^N E_2^2(n\Delta t - \epsilon) - \left(\sum_n^N E_2(N\Delta t - \epsilon)\right)^2}} \quad (4)$$

Here, N is the number of samples in the segment of the pulse echo that is scattered by the inhomogenity.

It is also possible to perform cross-correlation on quadrature detected output data which has been modulated with a carrier signal of frequency $f_0$. Let $Q_1(n\Delta t)$ be sampled quadrature data for the first echo and $Q_2(n\Delta t)$ be sampled quadrature data for the second echo. These echoes are written as follows:

$$Q_1(n\Delta t) = 0.5 \, A(n\Delta t) e^{j(\pi/2 + \theta(n\Delta t))} \quad (5)$$

$$Q_2(n\Delta t) = 0.5 \, A(n\Delta t + t_2 - t_1) e^{j(\pi/2 + 2\pi f_0(t - t_1) + \theta(n\Delta t + t_2 - t_1))} \quad (6)$$

The time shift $(t_2 - t_1)$ is equal to the value of $\epsilon$ for which $P_Q(\epsilon)$ is equal to unity. (* denotes the complex conjugate, | | denotes the absolute value, and the RE means "real part".)

$$P_Q(\epsilon) = \frac{RE\left[e^{j2\pi f_0\epsilon}\left(N\sum_n^N Q_1(n\Delta t)\,Q_2^*(n\Delta t - \epsilon) - \sum_n^N Q_1(n\Delta t)\sum_n^N Q_2^*(n\Delta t - \epsilon)\right)\right]}{\sqrt{N\sum_n^N |Q_1(n\Delta t)|^2 - \left|\sum_n^N Q_1(n\Delta t)\right|^2}\;\sqrt{N\sum_n^N |Q_2(n\Delta t - \epsilon)|^2 - \left|\sum_n^N Q_2(n\Delta t - \epsilon)\right|^2}}$$

This value of time shift $(t_2-t_1)$ is used in Equation (1) to obtain the magnitude of blood velocity at a given depth. Continuous segments of the first pulse are used in the cross-correlation to obtain a profile of the velocity of the blood as a function of depth. If the blood flow is fairly constant, subsequent profiles can be averaged to reduce statistical fluctuations on the profile.

Regardless of the particular method used for cross correlation, to measure high velocities at large depths, the effective $T_{PR}$ needs to be small as far as flow measurement is concerned and $T_{PR}$ needs to be large as far as the double transmit time through the tissue is concerned. An effective short $T_{PR}$ can be obtained by combining two coded pulses at the transmitter with a predetermined delay. It is this predetermined delay which is the effective $T_{PR}$ for flow measurement purposes. It must be noted that, because of the composite structure of the two coded pulses, the two pulses cannot be distinguished at the transmitter because they are expanded in time by coding. On the other hand, after match filtering the width of the pulses reduces at the receiver, and hence the two pulses can be separated in time. It is then the cross correlation of these two separated pulses which yields the quantity $(t_2-t_1)$ in equation (1).

A method of decoding the pulses according to a preferred embodiment of the present invention utilizes matched filters. Matched filters have two basic characteristics. First, if a signal spectrum is described by $S(\omega)$, a frequency response function of a filter that results in a maximum signal-to-noise ratio at the filter output is the complex conjugate of the spectrum, $S^*(\omega)$. Second, if a signal waveform is defined by $s(t)$, where t is time, an impulse response of the filter meeting the first characteristic is $s(-t)$, and the filter output waveform is found by performing the operation:

$$p(t) = \int_{-\infty}^{\infty} s(\tau)s(t-\tau)d\tau. \tag{8}$$

For purposes of illustration, coded pulses will now be discussed. A linear-FM matched-filter pulse is given by the following expression, where $\omega_0 = 2\pi f_0$ is an angular carrier frequency, t is time, $\Delta f$ is a signal bandwidth, T is a pulse duration, and $\mu = 2\pi\Delta f/T$.

$$S_{LFM+}(t) = \text{rect}\left[\frac{t}{T}\right]\cos\left[\omega_0 t + \frac{\mu t^2}{2}\right] \tag{9}$$

$$\text{rect}(x) = \begin{array}{l} 1\ |x| \leq \frac{1}{2} \\ 0\ |x| > \frac{1}{2} \end{array} \tag{10}$$

The "+" sign indicates that the frequency of the linear-FM matched filter pulse increases linearly with time. For this pulse, the frequency spectrum is given approximately by the following expression:

$$S_{LFM+}(\omega) \approx \sqrt{\frac{2\pi}{\mu}}\,\text{rect}\left[\frac{(\omega-\omega_0)}{\Delta\omega}\right]e^{-\frac{j(\omega-\omega_0)^2}{2\mu}} \tag{11}$$

The frequency spectrum of the matched filter required for the decoding of Equation (9) is therefore of the form:

$$H_{LFM+}(\omega) = e^{\frac{j(\omega-\omega_0)^2}{2\mu}} \tag{12}$$

and the decoded signal $P_{LFM}(t)_+$ is found by an inverse Fourier transform of the product $S_{LFM+}(\omega)\cdot H_{LFM+}(\omega)$.

$$P_{LFM+}(t) \approx \sqrt{T\Delta f}\,\text{rect}\left[\frac{t}{2T}\right]\cos(\omega_0 t)\text{sinc}(\Delta f t) \tag{13}$$

At its maximum, the decoded signal $P_{LFM}(t)$ is <u>larger</u> than the original signal $S_{LFM}(t)$ by a factor $\sqrt{T\Delta F}$, which is called the processing gain. This gain is usually expressed on the dB scale into the form $10\log_{10}(T\Delta f)$. This is the factor by which the signal-to-noise ratio of the signal is improved.

The linear-FM matching filter pulse of Equation (9) shows a frequency increase as a function of time. This will be designated as a positive coded pulse. A linear-FM pulse matched filter pulse can be written for which the frequency decreases linearly as a function of time. This will be designated as a negative coded pulse.

$$S_{LFM-}(t) = \text{rect}\left[\frac{t}{T}\right]\cos\left[\omega_0 t - \frac{\mu t^2}{2}\right]. \tag{14}$$

This negative coded pulse has a frequency spectrum given approximately by:

$$S_{LFM-}(\omega) \approx \sqrt{\frac{2\pi}{\mu}}\,\text{rect}\left[\frac{(\omega-\omega_0)}{\Delta\omega}\right]e^{\frac{j(\omega-\omega_0)^2}{2\mu}} \tag{15}$$

and the matched filter required for the decoding of equation (14) has the frequency spectrum:

$$H_{LFM-}(\omega) = e^{\frac{-j(\omega-\omega_0)^2}{2\mu}} \tag{16}$$

The decoded signal $P_{LFM-}(t)$ is found by an inverse Fourier transform of the product $S_{LFM-}(\omega)\cdot H_{LFM}(\omega_-)$.

The decoded waveforms have similar pulse shapes and processing gains. If both coded pulses in the combined form are fed to one of the matched filters, a processing gain for the pulse to which that filter matches only is attained, and the other pulse merely goes through the matched filter without any additional gain. As a results of match filtering the expanded pulse is compressed in time and it is for this reason that the two pulses after decoding or matched filtering can be separated in time. The amount of reduction in the width of the pulse is given by the time bandwidth product at the matched filters; that is $T\Delta f$.

Equations (9)-(16) hold for signals transmitted without distortion. In an actual system, the decoded signal pulse is an inverse Fourier transform of the product $S(\omega)H(\omega)T(\omega)$ where $T(\omega)$ is the transfer function of the system. If $T(\omega)$ is significantly different from unity, the decoding will not be optimal. However, coded pulses transmitted by a system having a realistic transfer function can be cross-correlated successfully.

Figure 3:
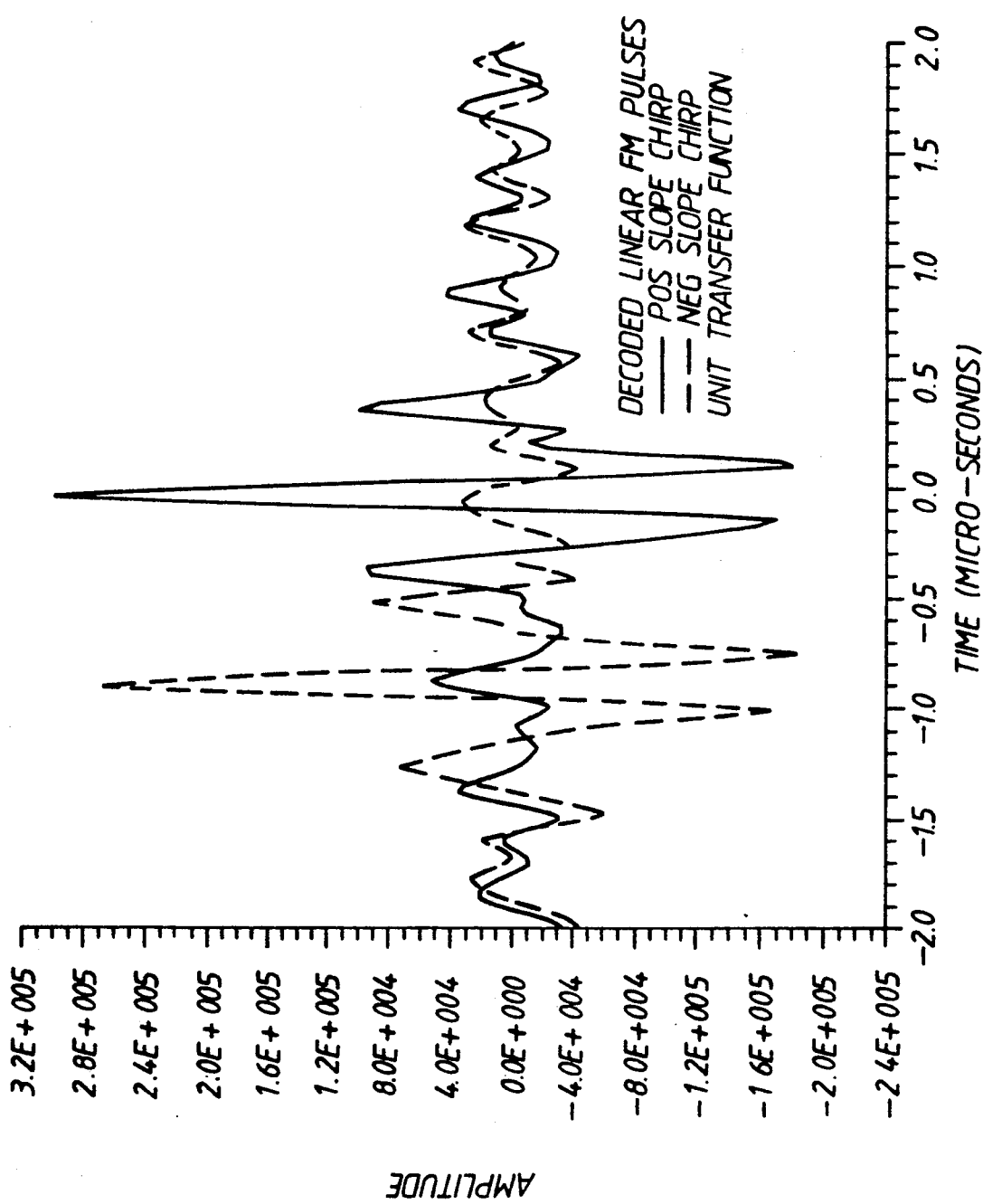
FIG. 3 is a graph illustrating the decoding of oppositely coded, linear-FM pulses that have been transmitted 0.9 microseconds apart.
Figure 4:
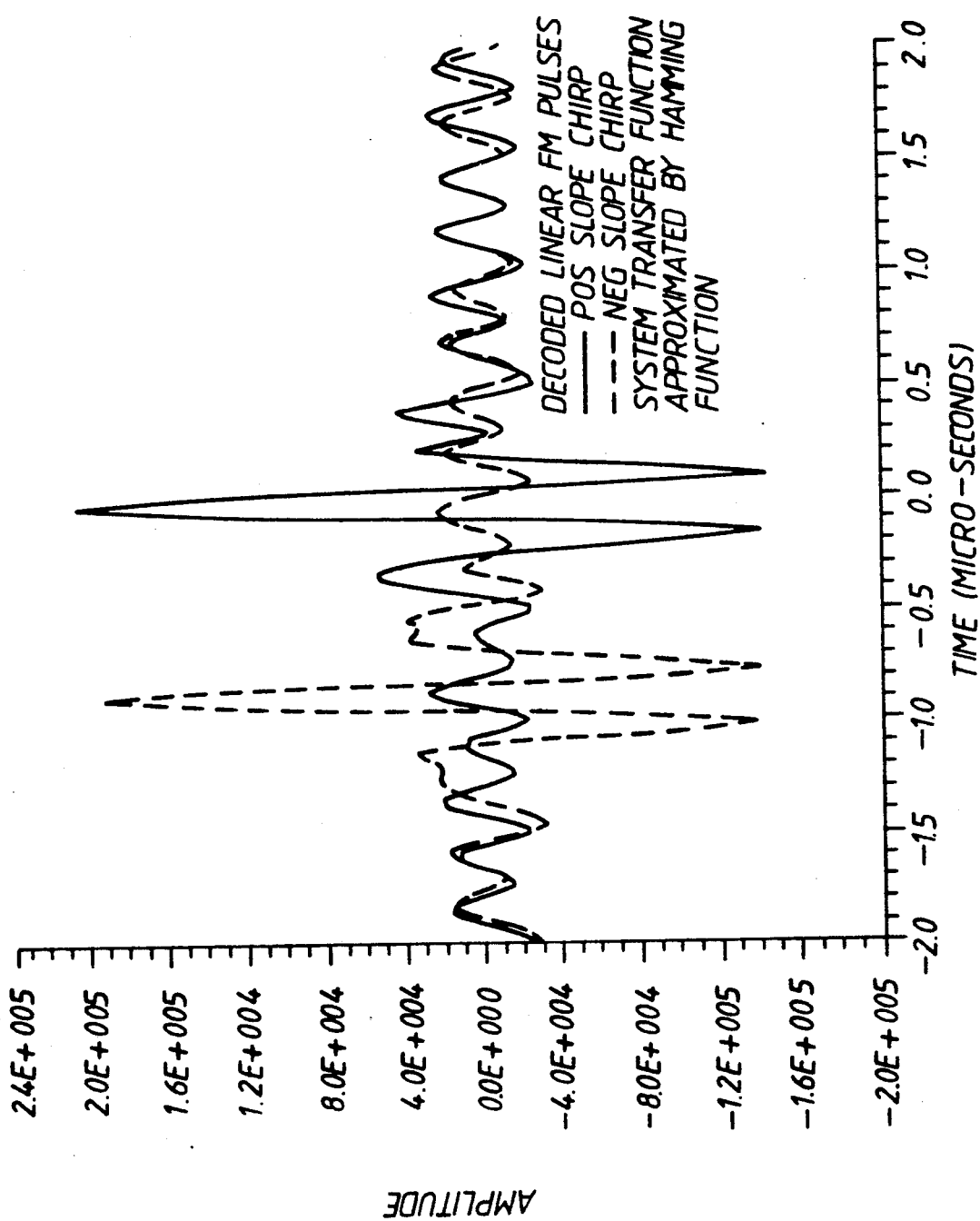
FIG. 4 is a graph illustrating the decoding of oppositely coded, linear-FM pulses that have been transmitted 0.9 microseconds apart, the transfer function for the velocimeter is approximated by a Hamming function.

FIGS. 3 and 4 illustrate the effect the transfer function can have on linear-FM coded pulses. By way of illustration, the system transfer function is assumed to be approximated by a Hamming function. These figures simulate linear-FM chirp, ultrasound pulses reflected from three stationary point objects. In both FIGS. 3 and 4, the dashed line represents the decoded, negative linear-FM pulse and the solid line represents the decoded, positive linear-FM pulse. The pulses have a duration $T=27$ μseconds, but are transmitted only 0.9 μseconds apart, so that they are superimposed during transmission. The center frequency is $f_0=4$ MHz, and the bandwidth is $\Delta f=4$ MHz. These illustrations have a discrete sampling interval of 0.03 μseconds.

FIG. 3 shows the ideal decoded signals. The gain of the matched pulse over the background is about 20 dB. If the pulses were identical, the cross-correlation coefficient match between the two pulses would be perfect and the cross-correlation coefficient would be 1.0. In practice, however, a cross-correlation coefficient of approximately 0.7 or higher is adequate for determining flow velocity profiles. The cross-correlation coefficient between the two pulses in FIG. 3 is about 0.96.

FIG. 4 shows the signals when a Hamming filter is used to simulate the system transfer function. The gain has been reduced to about 17 dB as a result of the Hamming filter. However, the cross-correlation coefficient is still about 0.95.

In the above discussion the principal operation of the coding inputs for the purpose of cross-correlation flow measurement was given. It is known, however, that when the echo arrives from a moving target the code on the reflected echo can be disturbed. The change in the code is primarily due to the Doppler effect. For an object approaching a transducer with a velocity v in a medium where the speed of sound is c, all the frequency components in the spectrum of the echo are multiplied by a factor of $(1+u)$ where $u=2v/c$. Similarly, if the object is moving away from the transducer, all the frequency components are downshifted in frequency. For a blood flow velocity as high as 10 m/s and a c of 1550 m/s, u turns out to be 0.013 which although small, can cause problems in decoding.

Because of these problems, a preferred embodiment of the present invention utilizes nonlinear chirp pulses, such as a hyperbolic-FM signals $S_{HFM\pm}(t)$. These signals have the form:

$$S_{HFM\pm}(t) = \text{rect}\left[\frac{t}{T}\right]\cos\left[\frac{\omega_0^2}{\mu}\ln\left[1\pm\frac{\mu t}{\omega_0}\right]\right] \quad (17)$$

The frequency spectra of these waveforms are given by:

$$S_{HFM\pm}(\omega) = \frac{\omega_0}{\omega}\sqrt{\frac{2\pi}{\mu}}\,\text{rect}\left[\frac{\omega_0}{\Delta\omega}(\omega_0/\omega - 1)\right]e^{-\frac{j\omega(\omega-\omega_0)}{\pm\mu}}e^{-\frac{j\omega_0^2}{\pm\mu}\ln(\omega_0/\omega)} \quad (18)$$

The decoding filters have the form:

$$H_{HFM\pm}(\omega) = e^{-\frac{j(\omega-\omega_0)\omega}{\pm\mu}}e^{\frac{j\omega_0^2}{\pm\mu}\ln(\omega_0/\omega)} \quad (19)$$

When a hyperbolic-FM waveform is transmitted and reflected from a moving target, and, if the received signal is decoded in the matched filter, the resulting output signal $S_{HFM}^R(\omega_\pm)$ containing only the time-shifted term and the phase-shifted terms is given by:

$$S_{HFM\pm}^R(\omega) \approx \quad (20)$$

$$C\,\text{rect}\left[\frac{\omega_0}{\Delta\omega}\left[\frac{\omega_0}{(1+u)\omega} - 1\right]\right]e^{-\frac{ju\omega\omega_0}{\pm\mu}}e^{\frac{j\omega_0^2}{\pm\mu}\ln(1+u)}$$

Figure 5:
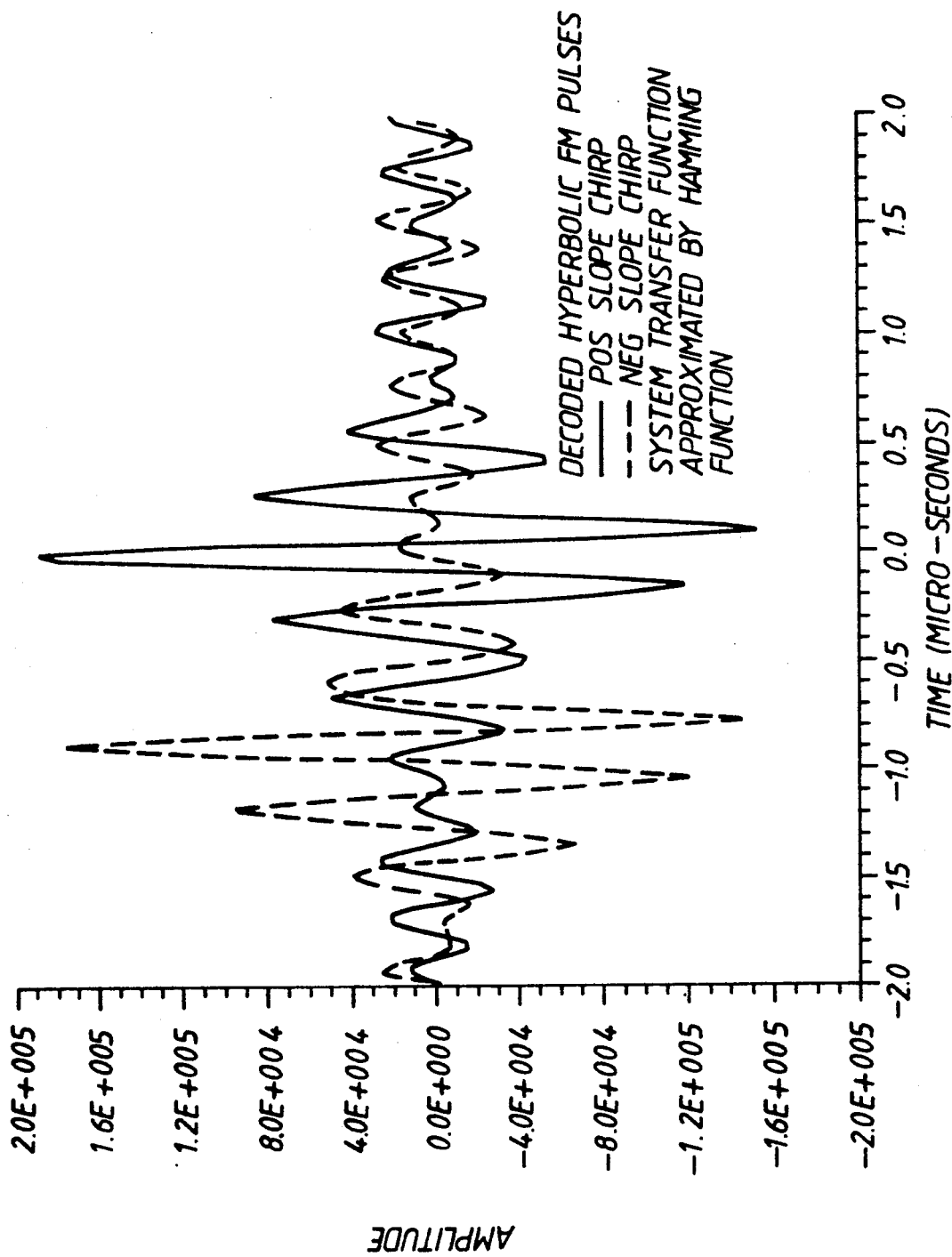
FIG. 5 is a graph illustrating the decoding of oppositely coded hyperbolic-FM pulses that have been transmitted 0.9 microseconds apart, the transfer function for the velocimeter is approximated by a Hamming function.

FIG. 5 illustrates the use of the hyperbolic-FM coded pulses. The conditions of FIG. 4 apply except that the hyperbolic-FM pulses and their matched filters are used instead of the linear-FM pulses. The Hamming filter is used to simulate the system transfer function. When employing hyperbolic FM pulses, the sidelobes are higher than those obtained by linear FM pulses, as can be seen from FIG. 5. The processing gain is also marginally lower than that attainable with the linear FM pulses. The cross correlation coefficient for this case is approximately 0.97.

Figure 6:
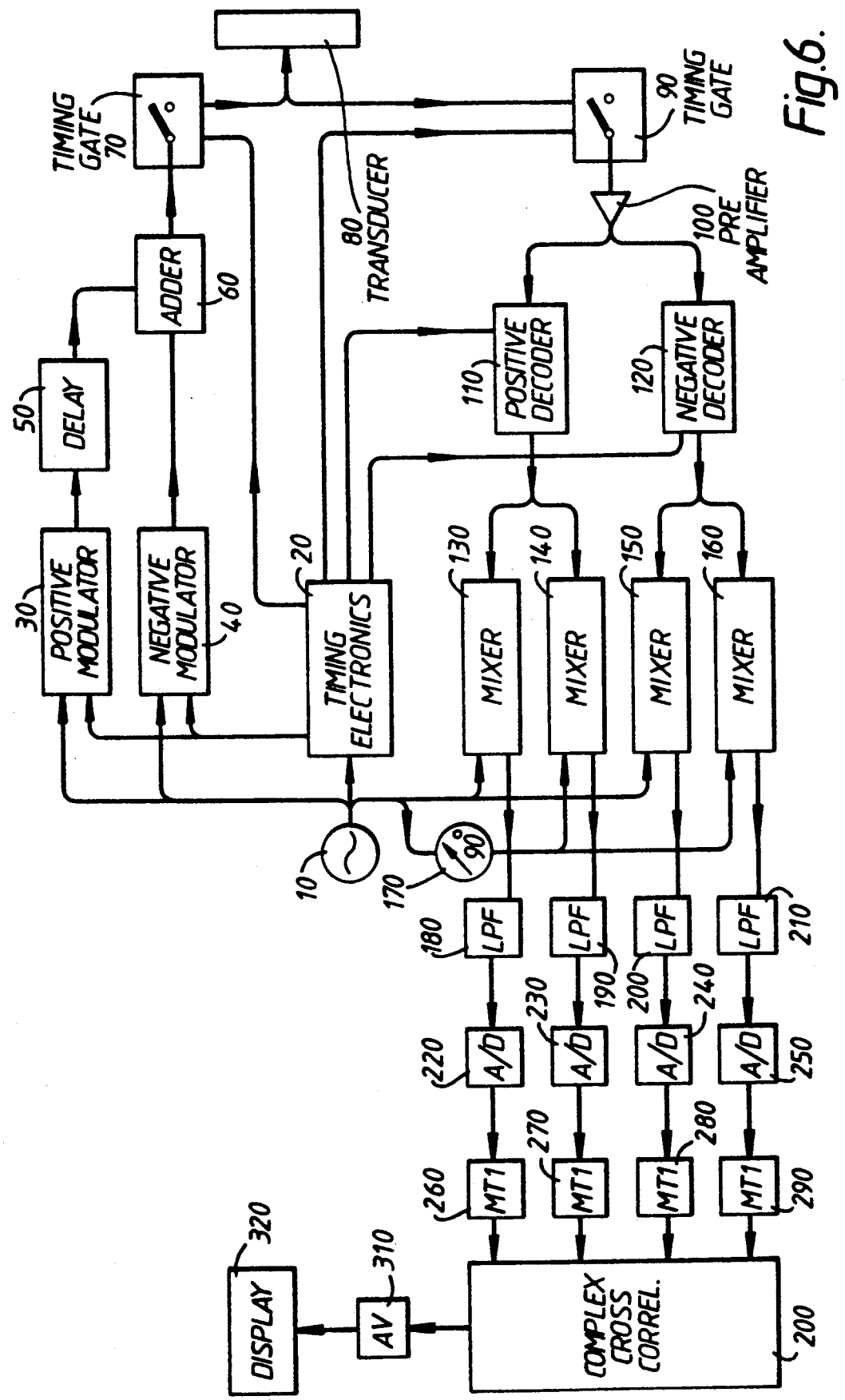
FIG. 6 is a functional block diagram illustrating a preferred embodiment of an ultrasound high velocity flow measurement apparatus using time domain correlation.

A functional block diagram of a preferred embodiment of an ultrasound high velocity flow measurement apparatus using time domain correlation is shown in FIG. 6. According to the present invention, oscillator 10 is connected to timing electronics 20, positive modulator 30, negative modulator 40, and mixers 130, 140, 150 and 160. Timing electronics 20 is connected to positive modulator 30, negative modulator 40, timing gate 70, timing gate 90, positive decoder 110 and negative decoder 120. Negative modulator 40 and positive modulator 30, connected through delay component 50, are connected to adder 60 which, in turn, is connected to time gate 70. The signal from time gate 70 is applied to the transducer 80.

The signal received from time gate 90 is sent to the preamplifier 100, which in turn is connected to positive decoder 110 and negative decoder 120. Positive decoder 110 is connected to mixers 130 and 140. Negative decoder 120 is connected to mixers 150 and 160. Mixer 130 is connected to low pass filter 180 and is driven by oscillator 10. Mixer 140 is connected to low pass filter 190 and to phase shifter 170. Phase shifter 170 introduces 90° phase shift to the signal from oscillator 10. Mixer 150 is connected to low pass filter 200 and is fed from oscillator 10. Mixer 160 is connected to low pass filter 210 and to shifter 170. Low pass filters 180, 190, 200 and 210 are connected to A/D converters 220, 230, 240 and 250, respectively. A/D converters 220, 230, 240 and 250 are connected to moving target indicators 260, 270, 280 and 290, respectively. Moving target indicators 260, 270, 280 and 290 are connected to the input of complex cross-correlator 300. A presently preferred embodiment provides that the output of complex cross-correlator 300 is connected to averager 310; however, the system can be used without the averager. The output of averager 310 is connected to display 320.

Although no imaging system is shown, the velocimeter of the present invention also can be combined with imaging electronics to produce two dimensional flow images for color flow mapping. The combining of the velocimeter of the present invention with imaging electronics is considered to be apparent to those skilled in the art of color flow mapping.

Operation of the invention will now be explained with reference to the preferred embodiment illustrated in FIG. 6. A carrier signal is generated by free running oscillator 10. The carrier signal produces a reference signal used by positive modulator 30, negative modulator 40, and mixers 130, 140, 150 and 160. Timing electronics 20 produces control signals for modulators 30 and 40, for demodulators 110 and 120, and for two time gates 70 and 90. Positive modulator 30 produces a positive hyperbolic-FM pulse which corresponds to the (+) form of Equation (17). This pulse is delayed by a time interval $\tau$ determined by delay component 50. Negative modulator 40 produces a negative hyperbolic-FM pulse which corresponds to the (−) form of Equation (17). The delayed, positive hyperbolic-FM pulse is combined with the negative hyperbolic-FM pulse by adder 60.

At appropriate intervals determined by timing electronics 20, both the delayed, the positive and the negative hyperbolic-FM coded pulses are passed by time gate 70 and are applied to transducer 80. The transducer transmits an ultrasound beam with dual time coding into the medium. After a time interval corresponding to a round trip to and from the moving blood, timing electronics 20 opens timing gate 90, allowing composite echoes comprising echo pulses of both the delayed, positive and the negative coded pulses, to pass into pre-amplifier 100 and then into positive decoder 110 and negative decoder 120. Positive decoder 110 effects convolution with a waveform having the frequency spectrum of the (+) form of Equation (19). Negative decoder 120 effects convolution with a waveform having the frequency spectrum of the (−) form of Equation (19). The output of positive decoder 110 is a compressed pulse of the form of the solid line in FIG. 5. The output of negative decoder 120 is a compressed pulse of the form of the dashed line in FIG. 5. These decoded pulses will be separated in time by the interval $\tau$ plus any time shift $(t_2-t_1)$ caused by the motion of the blood.

Both decoded pulses undergo quadrature detection. The output from positive decoder 110 is fed to both mixer 130 and mixer 140. The output from negative decoder 120 is fed to both mixer 150 and mixer 160. Mixer 130 multiplies the output from positive decoder 110 by the carrier signal produced by oscillator 10 to produce the real part of Equation (5). This signal is filtered by low-pass filter 180, sampled by A/D converter 220, passed through moving-target indicator 260 and fed to complex cross-correlator 300. Mixer 140 multiplies the signal from positive decoder 110 by the 90° phase shifted carrier signal output from shifter 170 to produce the imaginary part of Equation (5). This signal is filtered by low-pass filter 190, sampled by A/D converter 230, passed through moving-target indicator 270 and input to complex cross correlator 300. Mixer 150 multiples the output from negative decoder 120 by the carrier signal produced by oscillator 10 to produce the real part of Equation (6). This signal is filtered by low-pass filter 200, sampled by A/D converter 240, passed through moving-target indicator 280 and input to complex cross correlator 300. Mixer 160 multiplies the output from negative decoder 120 by the phase shifted carrier signal output from shifter 170 to produce the imaginary part of Equation (6). This signal is filtered by low-pass filter 200, sampled by A/D converter 260, passed through moving-target indicator 290, and input to complex cross-correlator 300. The complex cross-correlator 300 outputs the velocity profile given by Equation (1) as a function of depth. This profile passes into averager 310 for averaging, if desired, and then to display 320.

The present invention may, therefore, be summarized as providing an ultrasound high velocity flow measurement apparatus using cross-correlation between consecutive echoes of coded pulses to determine velocity profiles of flowing blood. The interval between at least two coded pulses can be made arbitrarily small, and thus can remove the peak velocity limitation. Furthermore, the present invention improves the signal-to-noise ratio over that obtainable by use of uncoded pulses.

It will be apparent to those skilled in the art that modifications and variations can be made in the ultrasound high velocity flow correlation measurement apparatus of the present invention. The invention in its broader aspects is, therefore, not limited to the specific details, representative methods and apparatus, and illustrated examples shown and described herein. Thus, it is intended that all matter contained in the foregoing description and shown in the accompanying drawings shall be interpreted as illustrative and not in a limiting sense.

What is claimed is:

1. An ultrasound high velocity flow measurement apparatus using time domain correlation, comprising:
    oscillator means for producing a carrier signal;
    modulator means for producing at least two different coded pulses, using as a reference signal the carrier signal produced by the oscillator means, the at least two different coded pulses being separated by a predetermined delay, the modulator means including adding means for adding the at least two different coded pulses being separated by a predetermined delay;
    transducer means for transmitting the added at least two different coded pulses to a moving object;
    receiving means for receiving a returned echo signal from the moving object;
    decoding means for decoding the returned echo signal and producing at least two decoded signals being separated by the predetermined delay; and
    correlation means for cross-correlating the two decoded signals and outputting a velocity flow measurement of the moving object.

2. The apparatus as recited in claim 1, wherein the modulator means includes a positive modulator means for producing a positive-slope Doppler-insensitive coded pulse and a negative modulator means for producing a negative-slope Doppler-insensitive coded pulse.

3. The apparatus as recited in claim 2, wherein the modulator means includes a delay means for delaying the positive-slope Doppler-insensitive coded pulse by the predetermined delay.

4. The apparatus as recited in claim 1, wherein the at least two different coded pulses are linear-FM coded pulses.

5. The apparatus as recited in claim 1, wherein the at least two different coded pulses are hyperbolic-FM or nonlinear FM coded pulses.

6. The apparatus as recited in claims 1, wherein the receiving means includes a timing gate for forwarding the returned echo signal from the receiving means to the decoding means after a predetermined time interval.

7. The apparatus as recited in claim 6, wherein the receiving means includes a pre-amplifier for amplifying the returned echo signal.

8. The apparatus as recited in claim 1, wherein the decoding means includes a positive decoder for decoding the amplified returned echo signal having a positive slope and outputting a decoded positive signal and a negative decoder for decoding the returned echo signal having a negative slope and outputting a decoded negative signal.

9. The apparatus as recited in claim 8, wherein the decoding means includes two mixers connected to the positive decoder, wherein one of the two mixers multiplies the positive decoded signal by the carrier signal and one of the two mixers multiplies the positive decoded signal by a 90° phase-shifted carrier signal and two mixers connected to the negative decoder, wherein one of the two mixers multiplies the negative decoded signal by the carrier signal and one of the two mixers multiplies the negative decoded signal by a 90° phase-shifted carrier signal, low pass filters connected to each of the mixers for filtering each of the signals produced by each of the mixers, A/D converters connected to each low pass filter for converting to a digital signal each filtered signal from each of the low pass filters, and moving target indicators connected to each A/D converter for flow mapping processing of each of the digital signals.

10. The apparatus as recited in claim 1, wherein the correlation means includes an averager for averaging the decoded signals, and a display for displaying the velocity flow measurement of the moving object.

11. A method of measuring high velocity flow utilizing an ultrasound high velocity flow measurement apparatus using time domain correlation, comprising the steps of:
producing at least two different coded pulses, the at least two different coded pulses being separated by a predetermined delay;
transmitting the at least two different coded pulses to a moving object;
receiving a returned echo signal from the moving object;
decoding the returned echo signal and producing at least two decoded signals being separated by the predetermined delay; and
cross-correlating the two, decoded signals and outputting a velocity flow measurement of the moving object.

12. The method of claim 11, wherein the step of producing at least two different coded pulses includes producing a positive hyperbolic-FM pulse and a negative hyperbolic-FM pulse.

13. The method of claim 11, wherein the step of producing at least two different coded pulses includes producing a positive quadratic-FM pulse and a negative quadratic-FM pulse.

14. The method of claim 11, wherein the step of decoding the returned echo signal includes quadrature detection.

* * * * *